United States Patent [19]

Suzuki

[11] Patent Number: 5,163,423
[45] Date of Patent: Nov. 17, 1992

[54] HUMIDIFIER

[75] Inventor: Shiro Suzuki, Bunkyo, Japan

[73] Assignee: Origin Medical Instrument Co., Ltd., Tokyo, Japan

[21] Appl. No.: 800,099

[22] Filed: Nov. 29, 1991

[30] Foreign Application Priority Data

Nov. 30, 1990 [JP] Japan ................. 2-329421

[51] Int. Cl.$^5$ ............... A61M 16/16; A61M 16/18
[52] U.S. Cl. .................. 128/203.26; 128/207.14; 128/204.17; 128/205.23; 236/44 A
[58] Field of Search ............ 128/203.26, 203.27, 128/204.17, 203.16, 203.17, 207.14, 205.23; 236/44 A

[56] References Cited

U.S. PATENT DOCUMENTS

| | | | |
|---|---|---|---|
| 2,020,484 | 11/1935 | Turner | 272/58 G |
| 2,143,795 | 1/1939 | Okey | 236/44 A |
| 3,251,361 | 5/1966 | Rusz | 128/203.27 X |
| 3,923,057 | 12/1975 | Chalon | 128/203.16 |
| 4,051,205 | 9/1977 | Grant | 128/203.27 X |
| 4,291,487 | 9/1981 | Magid | 273/58 E |
| 4,564,748 | 1/1986 | Gupton | 128/204.17 X |
| 4,610,071 | 9/1986 | Miller | 273/58 A |
| 4,621,632 | 11/1986 | Bartels et al. | 128/203.17 X |
| 4,682,010 | 7/1987 | Drapeau et al. | 128/204.17 X |
| 4,708,831 | 11/1987 | Elsworth et al. | 128/203.17 X |
| 4,722,334 | 2/1988 | Blackmer et al. | 128/203.17 X |
| 4,852,363 | 8/1989 | Kampf et al. | 236/44 A X |

FOREIGN PATENT DOCUMENTS 21299 of 1894 United Kingdom .............. 273/58 E

Primary Examiner—Vincent Millin
Assistant Examiner—Sebastiano Passaniti
Attorney, Agent, or Firm—Evenson, Wands, Edwards, Lenahan & McKeown

[57] ABSTRACT

A humidifier heats a gas to be supplied to a patient, for example, for anaesthesia in surgical operation or artificial respiration to cure difficulty of breathing, at an appropriate temperature and humidifies the same at an appropriate humidity. The humidifier calculates the absolute humidity on the basis of a set temperature and a set relative humidity by first calculating means, calculates the temperature of the gas corresponding to a saturation humidity equivalent to the calculated absolute humidity by second calculating means, controls a first heater for heating a humidifying chamber so that the temperature of the humidified gas at the outlet of the humidifying chamber coincide with the calculated temperature, and controls a second heater for heating the interior of a patient circuit connected to the outlet of the humidifier so that the temperature of the humidified gas at the outlet of the patient circuit conicides with the set temperature to prevent condensation within the patient circuit and the flow of water condensed in the patient circuit into the trachea of the patient who receives the humidified gas through the patient circuit. The humidifier is provided with display means for displaying the calculated absolute humidity to enable selection of an appropriate set temperature and an appropriate set relative humidity with reference to the absolute humidity displayed by the display means in order that the medical gas of an appropriate humidity is supplied to the patient.

2 Claims, 4 Drawing Sheets

HUMIDIFIER

BACKGROUND OF THE INVENTION

1. Field of the Invention

The present invention relates to a humidifier for properly humidifying a gas to be supplied to a patient for narcotization in surgical operation, for artificial respiration to cure the patient of difficulty of breathing or for oxygen inhalation.

2. Description of the Prior Art

Referring to FIG. 1 showing a conventional humidifier for such a purpose, a medical gas supplied by a respirator or an anaesthesia apparatus flows into a humidifying chamber 16' through the inlet 31 thereof as indicated by an arrow A, the medical gas heated and humidified in the humidifying chamber 16' flows out of the humidifying chamber 16' through an outlet 32 as indicated by an arrow B, and the heated and humidified medical gas is supplied to the patient through a patient circuit 17' having one end connected to the outlet 32 of the humidifying chamber 16' and the other end connected to the patient as indicated by an arrow 33. An air way temperature sensor 12' provided at the outlet of the patient circuit 17' detects the temperature of the medical gas. A heater 9' for heating the humidifying chamber 16' is controlled on the basis of the detection signal provided by the air way temperature sensor 12'.

Although the medical gas is heated and humidified properly in the humidifier, more specifically, by the humidifying chamber 16', dew drop occurs on the inner surface of the patient circuit 17'because, in most cases, the room temperature is lower than the temperature of the patient circuit 17', In the worst case, it is possible that water condensed in the patient circuit 17' flows into the trachea of the patient, risking the patient. Furthermore, some papers report that the degree of bacterial contamination of the interior of the pipe increases with the moisture in the pipe.

FIG. 2 shows another conventional humidifier incorporating improvements for eliminating the disadvantages of the humidifier shown in FIG. 1. This humidifier has a patient circuit 17' connecting a humidifying chamber 16' to a patient and internally provided with a heated wire 10' connected in parallel to a heater for 9' for heating the humidifying chamber 16'. The heated wire 10' heats the interior of the patient circuit 17' to prevent said dew drop within the patient circuit 17'. However, when the difference between the setting temperature and the room temperature is small, the medical gas is heated to the set temperature only by the heated wire 10'. In such case that the temperature of the humidifying water contained in the humidifying chamber 16' is low and the medical gas is heated to the set temperature by the heated wire 10', the relative humidity of the medical gas is reduced below an undesirable level.

As shown in FIG. 1 or FIG. 2, a temperature signal obtained by the temperature sensor 12' is displayed via the amplifier 25 and the digital display circuit 27.

Also both an output of the amplifier 25 and a signal from a temperature setting switch 29 are inputted to a temperature proportional control circuit 28.

An output signal of a circuit 28 can control the temperature of the heater 9' through an SSR 7'.

Further 18' and 19' are constructed as an electric source.

FIG. 3 shows a third conventional humidifier incorporating improvements to solve the foregoing problems. This humidifier is provided with a humidifying chamber temperature sensor 11' for detecting the temperature of the medical gas at the outlet of a humidifying chamber 16''. The output signal of the outlet temperature sensor for humidifying chamber 11' is applied through an amplifier 24 to a temperature proportional control circuit 28' for feedback control. A heater for humidifying chamber 9'for heating the humidifying chamber 16' is controlled so that the outlet temperature for the humidifying chamber, namely, the temperature of the gas at the outlet of the humidifying chamber 16', is in the range of a set temperature set by a temperature setting switch 29 plus 2° C. to plus 3° C. to compensate beforehand the moisture corresponding to the condensate that may be formed within a patient circuit 17''. In addition, a heated wire 10'' is controlled so that a temperature represented by the output signal of an air way temperature sensor 12' coincides with the set temperature.

In FIG. 3, an amplifier 23 corresponding to the amplifier 25 as shown in FIG. 1 or FIG. 2, and another amplifier 24 amplifying the signal obtained by a sensor 11' are inputted respectively to a digital display circuit 27 and a temperature proportional control circuit 28.

Further an SSR 7'' and a SSR 8'' are separated in function as shown in FIG. 1 and FIG. 2 respectively, and 10'' is shown as a heater.

However, condensation in the patient circuit 17'' is unavoidable because a gas of a saturated humidity flows through the patient circuit 17'', and the gas is cooled due to the difference between the temperature of the gas and the room temperature which is normally cooler than said gas. Although the quantity of condensate formed in the patient circuit 17'' of the third conventional humidifier is somewhat smaller than that of condensate formed in the patient circuit 17' of the first or second conventional humidifier, the performance of the third conventional humidifier is not satisfactory.

SUMMARY OF THE INVENTION

Accordingly, it is an object of the present invention to provide a humidifier capable of properly heating a gas to be supplied through a patient circuit to a patient for anaesthesia in surgical operation or for oxygen inhalation to cure difficulty of breathing and properly humidifying the same, and of ensuring security of the patient.

The humidifier heats and humidifies a medical gas in a humidifying chamber before supplying the medical gas through a patient circuit. It is possible that a large quantity of dew condensate may be formed in the patient circuit because the room temperature is lower than the temperature of the medical gas, and that the condensed water may flow into the trachea of the patient, risking the patient. On the contrary, the present invention provides a humidifier solving the foregoing problems, capable of securing an appropriate humidity within the patient circuit, capable of preventing dew drop within the patient circuit, improving safety, and simple in operation.

DESCRIPTION OF THE PREFERRED EMBODIMENT

A humidifier in a preferred embodiment according to the present invention is capable of satisfying both contradictory requirements, namely, securing a necessary humidity within a patient circuit and preventing condensation within the patient circuit.

Figure 1:
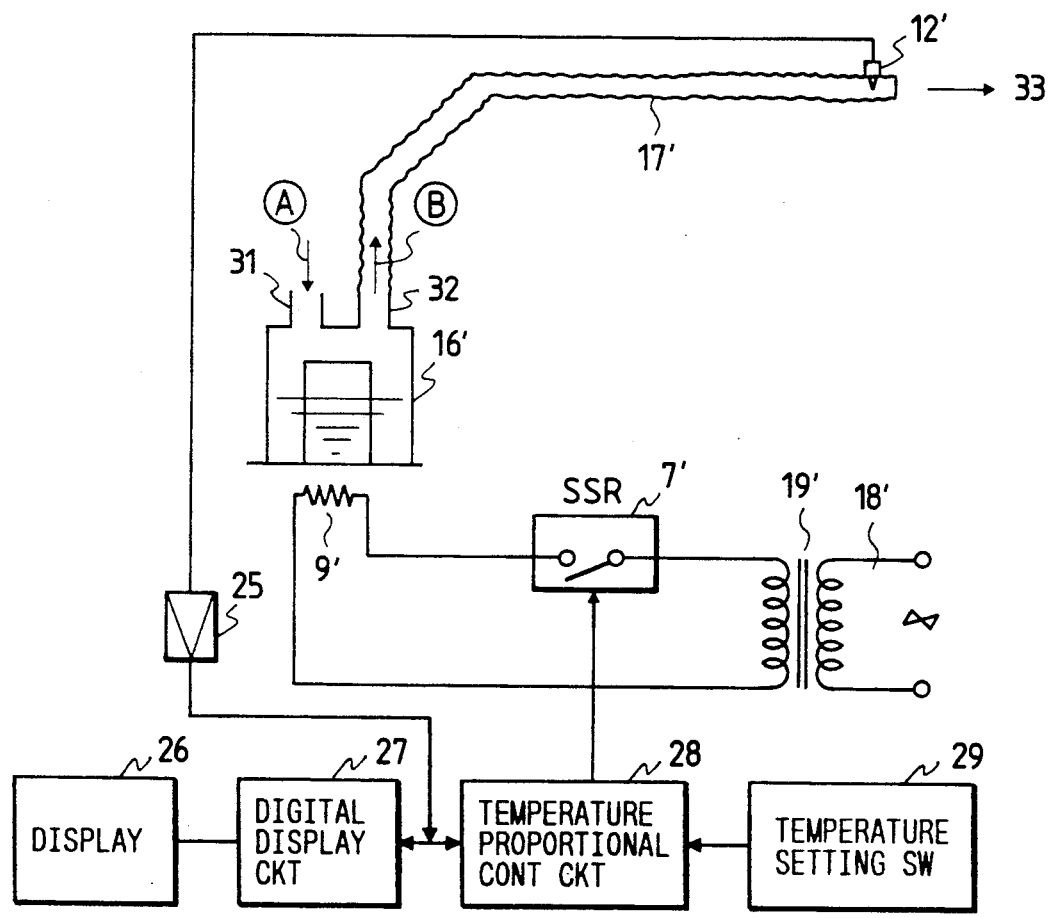
FIG. 1 is a block diagram of a first conventional humidifier for heating and humidifying a gas to be supplied to a patient for anaesthesia in surgical operation, for artificial respiration or for oxygen inhalation.
Figure 2:
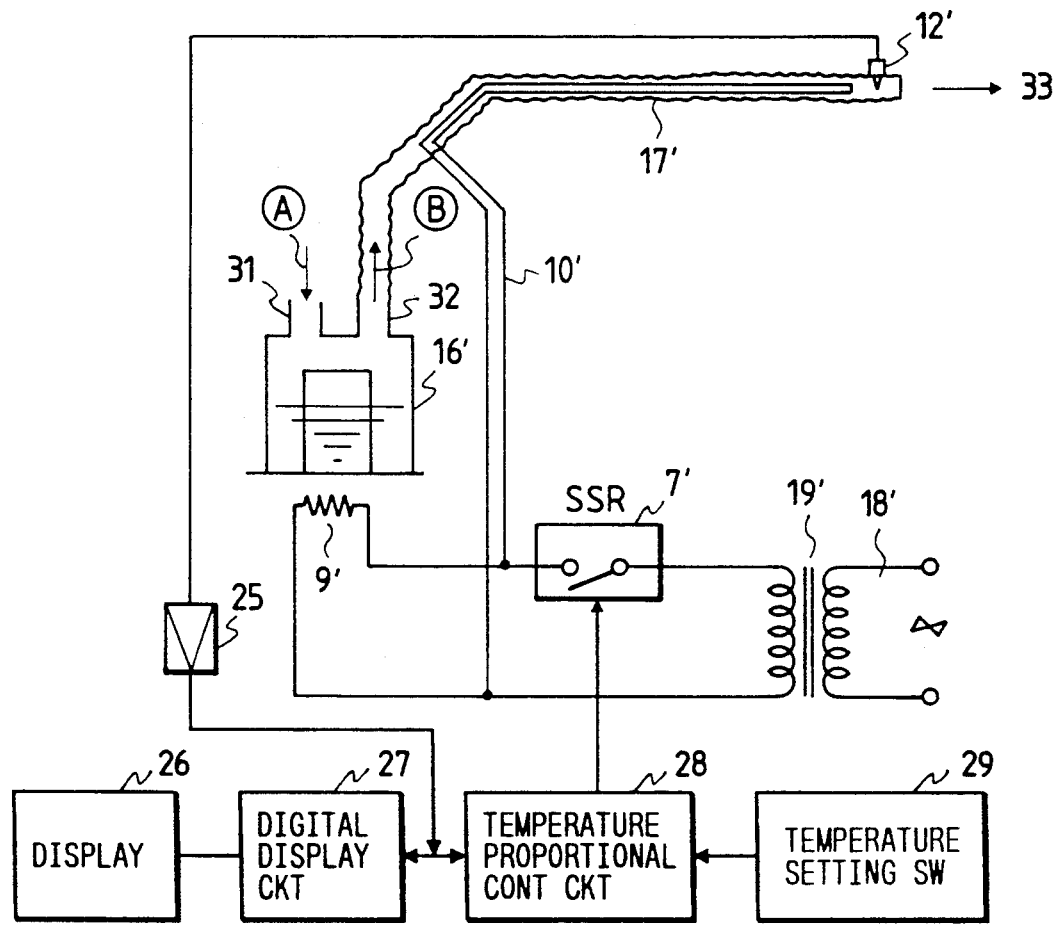
FIGS. 2 and 3 are block diagrams of second and third conventional humidifiers, similar to the humidifier shown in FIG. 1, additionally provided with a heated wire in a patient circuit.
Figure 3:
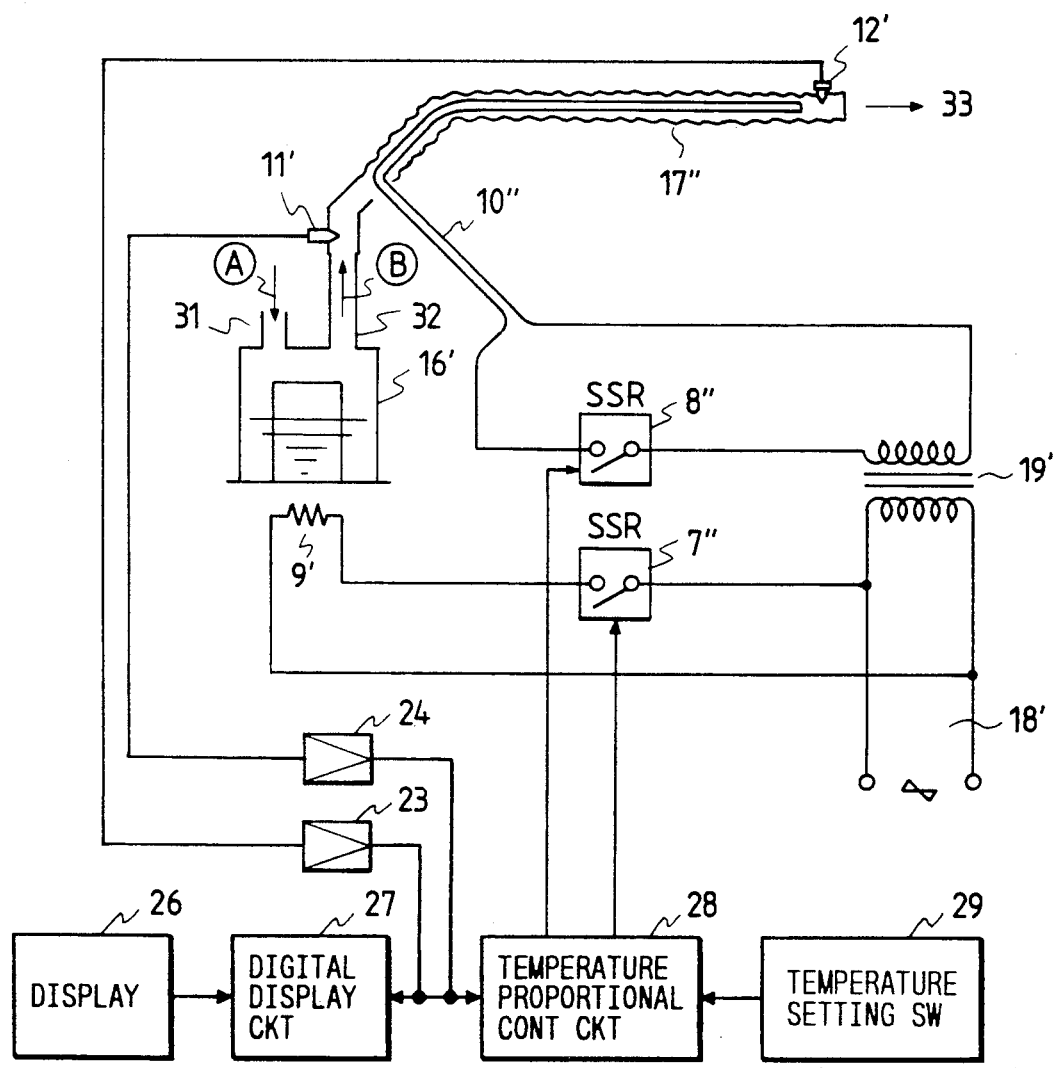
Figure 4:
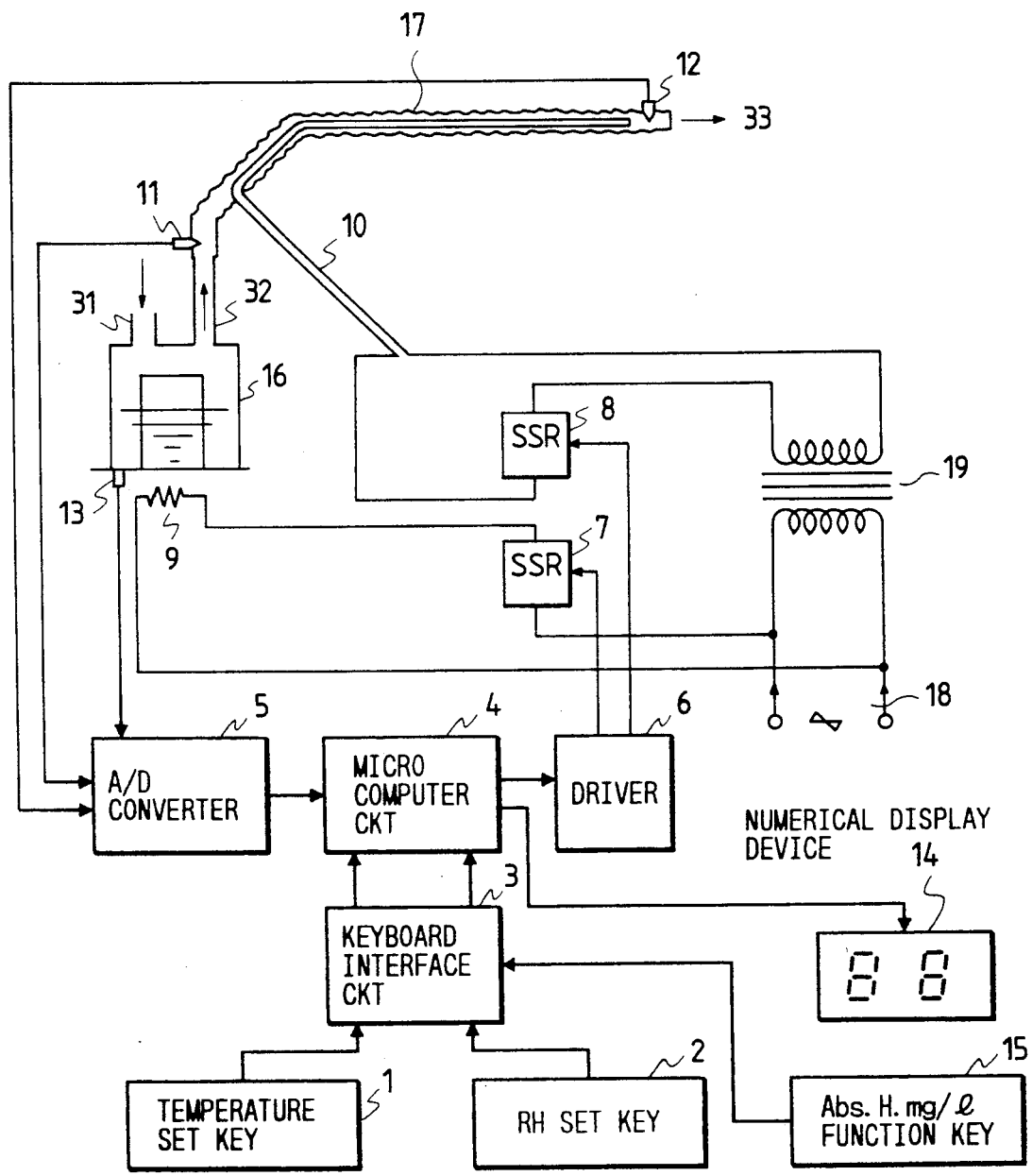
FIG. 4 is a block diagram of a humidifier in a preferred embodiment according to the present invention.

Referring to FIG. 4, a setting temperature is set by means of a temperature setting key 1, and a relative humidity (%) (hereinafter abbreviated to "RH") is set by means of a RH setting key 2. A desired RH is in the range of 70 to 80%.

An absolute humidity function key 15 is operated to display an absolute humidity (mg/e) (hereinafter referred to as "Abs. H") calculated on the basis of a set temperature set by means of the temperature setting key 1 and a set RH set by means of the RH setting key 2. When the absolute humidity function key 15 is operated, the calculated Abs. H is displayed immediately on a digital display 14. Normally, an appropriate Abs. H for a human organism is in the range of 30 to 35 mg/e. A necessary moisture content is determined on the basis of an Abs. H in the foregoing range.

When the set temperature is increased, the Abs. H must be increased to maintain the RH constant.

After values to be set beforehand have been set, the humidifier calculates an air temperature corresponding to a saturation humidity equivalent to the Abs. H, shown on a digital display. A microcomputer 4 gives a control signal to a driver 6 to control a humidifying chamber heater 9 through a solid state relay (SSR) 7 so that a temperature detected by a first temperature sensor for humidifying chamber 11 provided at the outlet of a humidifying chamber 16 coincides with the calculated temperature.

The microcomputer 4 gives a control signal to the driver 6 to control a heated wire 10 through a SSR 8 so that a temperature detected by an air way temperature sensor 12 provided at the outlet of a patient circuit 17 which coincides with the set temperature.

Thus, the RH of the air flowing through the patient circuit 17 is in the range of 70 to 80%, the temperature of the air at the outlet of the patient circuit 17 is equal to the set temperature, and the desired Abs. H is maintained. Since the RH of the air is normally in the range of 70 to 80% not 100%, condensation occurs scarcely within the patient circuit 17 even if the temperature of the patient circuit 17 is equal to the ambient temperature. The temperature of the air at the outlet of the patient circuit 17 is regulated at the set temperature, and a necessary Abs. H can be necessary enough humidity.

Designated at 13 is a temperature sensor to detect an over heating for a humidifying chamber, 3 designates a keyboard interface circuit for controlling in following two ways.

Furthermore, since the humidifier in accordance with the present invention is provided with calculating means for calculating the Abs.H on the basis of the set temperature and the set RH, and with display means for displaying the calculated Abs. H, it is very easy to decide if the desired Abs. H, as a function of the temperature and the RH, is appropriate to a human organism as compared with a standard Abs. H of, for , 30 mg/e, and air of an appropriate temperature and an appropriate moisture content can surely be supplied to the patient.

It is also possible to calculate the RH of air on the basis of a set temperature and a set Abs. H and display the calculated RH or to calculate the temperature of air on the basis of a set RH and a set Abs. H and display the calculated temperature, instead of calculating the Abs. H of air on the basis of a set temperature and a set RH and displaying the calculated Abs. H as in the foregoing embodiment.

That is, the first way is usually operated with the temperature set key 1 and the RH (%) set key 2 without such information signal as Abs.H.mg/e function key 15.

However, in the present invention, such construction with the Abs.H.mg/e function key 25 can be also achieved in the important operation as mentioned.

Although the present invention has been described in its preferred form with a certain degree of particularity, obviously many changes and variations are possible therein in the light of the above teachings. It is therefore to be understood that the present invention may be practiced otherwise than as specifically described herein without departing from the scope and spirit thereof.

What is claimed is:

1. A humidifier for humidifying a medical gas to be supplied to a patient comprising: a humidifying chamber having an outlet through which a humidified medical gas exits said chamber; a first heater for heating the humidifying chamber; a first temperature sensor for detecting the temperature of the medical gas at the outlet of the humidifying chamber, a patient circuit having an interior and an outlet through which the medical gas humidified in the humidifying chamber flows; a second heater for heating the interior of the patient circuit; and a second temperature sensor for detecting the temperature of the humidified medical gas at the outlet of the patient circuit; the improvement comprising:

first calculating means for calculating the absolute humidity (mg/e) of the humidified medical gas on the basis of a set temperature and a set relative humidity (%);

second calculating means for calculating the temperature of air corresponding to a saturation humidity equivalent to the calculated absolute humidity (mg/t); and control means for controlling said first heater for heating the humidifying chamber so that the temperature of the humidified medical gas at the outlet of the humidifying chamber coincides with the temperature calculated by the second calculating means.

2. A humidifier according to claim 1, further having a display device for displaying the absolute humidity (mg/e) calculated on the basis of said set temperature and said set relative humidity (%) by said first calculating means.

* * * * *